United States Patent [19]
Gordon

[11] Patent Number: 5,938,645
[45] Date of Patent: *Aug. 17, 1999

[54] PERCUTANEOUS ASPIRATION CATHETER SYSTEM

[75] Inventor: Lucas S. Gordon, Redmond, Wash.

[73] Assignee: Boston Scientific Corporation Northwest Technology Center Inc., Redmond, Wash.

[*] Notice: This patent is subject to a terminal disclaimer.

[21] Appl. No.: 08/822,364

[22] Filed: Mar. 20, 1997

Related U.S. Application Data

[63] Continuation-in-part of application No. 08/449,203, May 24, 1995, Pat. No. 5,827,229.

[51] Int. Cl.⁶ .................................................. A61M 29/00
[52] U.S. Cl. ............................ 604/264; 604/171; 604/35
[58] Field of Search .................................. 604/317, 319, 604/320, 322, 323, 22, 264, 280, 35, 39, 43, 53, 101, 113

[56] References Cited

U.S. PATENT DOCUMENTS

| | | |
|---|---|---|
| 4,573,966 | 3/1986 | Weikl et al. . |
| 4,646,736 | 3/1987 | Auth . |
| 4,729,763 | 3/1988 | Henrie ........................................ 604/22 |
| 4,894,051 | 1/1990 | Shiber . |
| 4,950,257 | 8/1990 | Hibbs ....................................... 604/265 |
| 5,034,005 | 7/1991 | Appling ................................... 604/280 |
| 5,084,013 | 1/1992 | Takase . |
| 5,234,403 | 8/1993 | Yoda et al. . |
| 5,346,569 | 9/1994 | Ikeda et al. . |
| 5,370,609 | 12/1994 | Drasler et al. . |
| 5,370,653 | 12/1994 | Cragg . |
| 5,395,332 | 3/1995 | Ressemann et al. . |
| 5,419,774 | 5/1995 | Willard et al. . |
| 5,451,233 | 9/1995 | Yock . |
| 5,476,450 | 12/1995 | Ruggio . |
| 5,527,292 | 6/1996 | Adams et al. . |

OTHER PUBLICATIONS

G.S. Reeder et al., Aspiration Thrombectomy For Removal Of Coronary Thrombus, The American Journal Of Cardiology, Jul. 1992; vol. 70, pp. 107–110.

J.K. Kahn et al., Thrombus Aspiration in Acute Myocardial Infarction Catheterization and Cardiovascular diagnosis, 1990, vol. 20, pp. 54–57.

Brown et al., Transcatheter Aspiration of Intracoronary Thrombus After Myocardial Infarction American Heart Journal, Sep. 1990, pp. 688–690.

Sniderman et al., Percutaneous Aspiration Embolectomy, The Journal of Cardiovascular Surgery, 1993, vol. 34, No. 3, pp. 255–257.

Guenther et al., Aspiration Catheter For Percutaneous Thrombectomy: Clinical Results, Radiology, Apr. 1990, vol. 175, No. 1, pp. 171–273.

Sniderman et al., Percutaneous Embolectomy by Transcatheter Aspiration Radiology, Feb. 1984, vol. 150, No. 2, pp. 357–361.

Turnipseed et al., Percutaneous Aspiration Thrombectomy (PAT): An Alternative to Surgical Balloon Techniques for Clot Removal, Journal of Vascular Surgery, 1986; vol. 3, pp. 437–441.

Greenfield et al., Transvenous Removal of Pulmonary Emboli by Vacuum–Cup Catheter Technique Journal of Surgical Research, 1969, pp. 347–352.

William J. Drasler, PhD., et al., Rheolytic Catheter For Percutaneous Removal of thrombus JORNAME: @ RADIOLOGY JAN. PAGE: 1 Sess: 3.

Primary Examiner—John G. Weiss
Assistant Examiner—David J. Cho
Attorney, Agent, or Firm—Todd P. Messal

[57] ABSTRACT

A percutaneous aspiration catheter removing thrombus or other emboli from blood vessels and a method of extracting embolus pieces larger than the diameter of the catheter. The percutaneous aspiration catheter has barbs positioned near its end to trap material within the catheter.

12 Claims, 10 Drawing Sheets

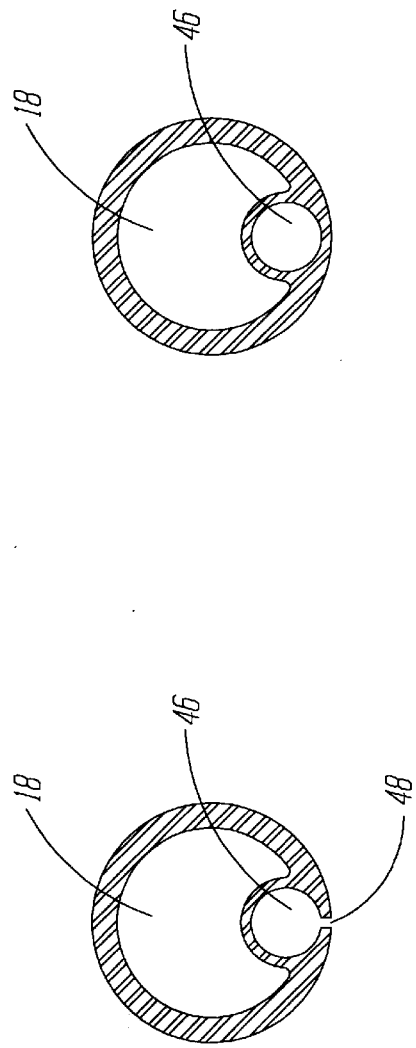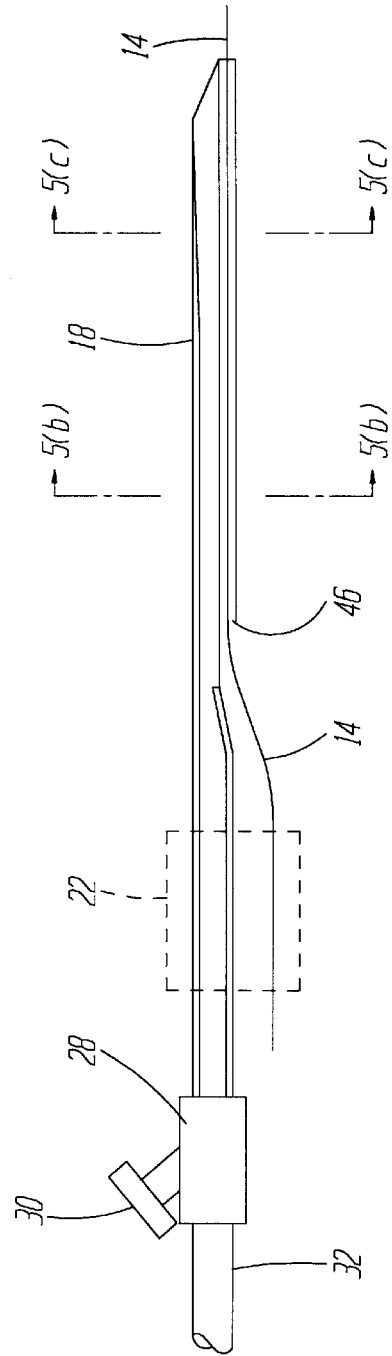

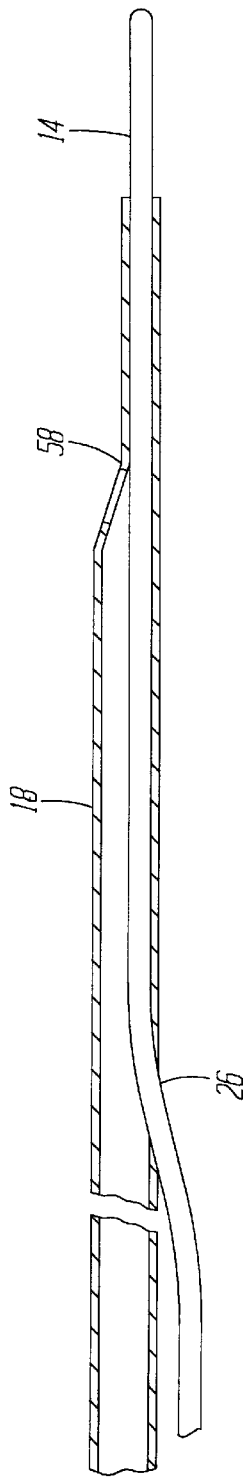
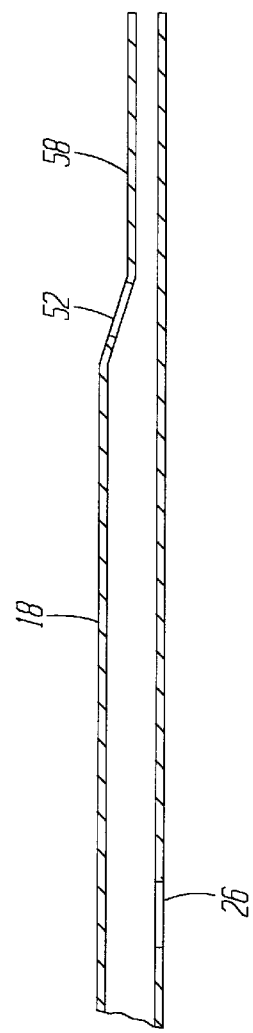
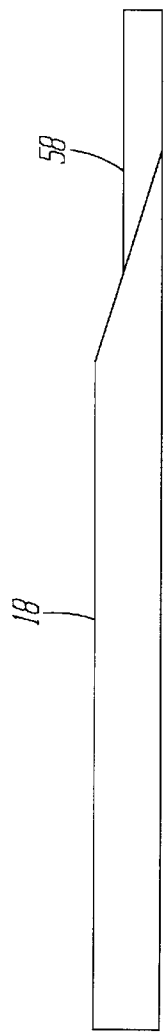
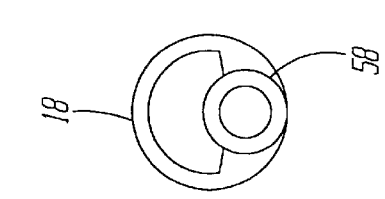
FIG. 7(a)
FIG. 7(b)
FIG. 7(c)
FIG. 7(d)

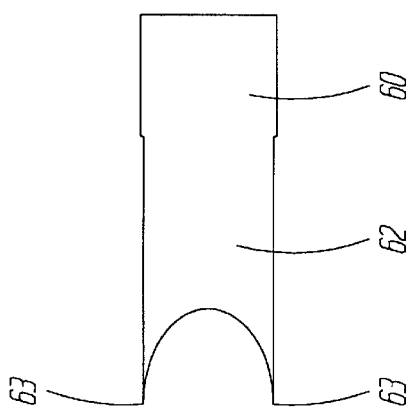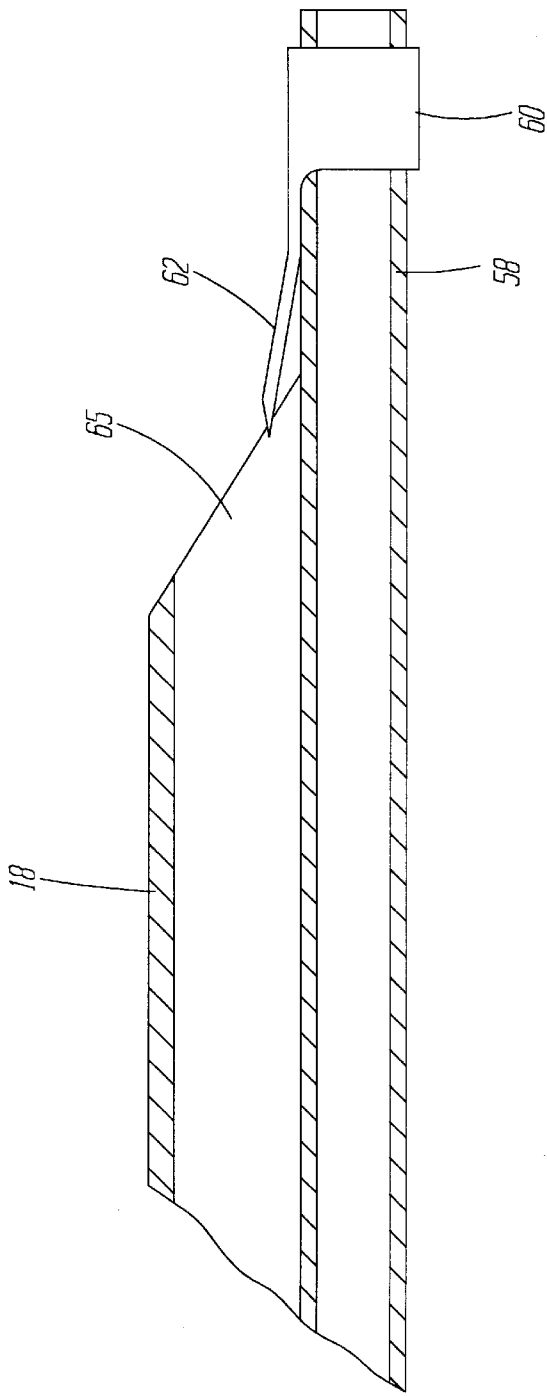

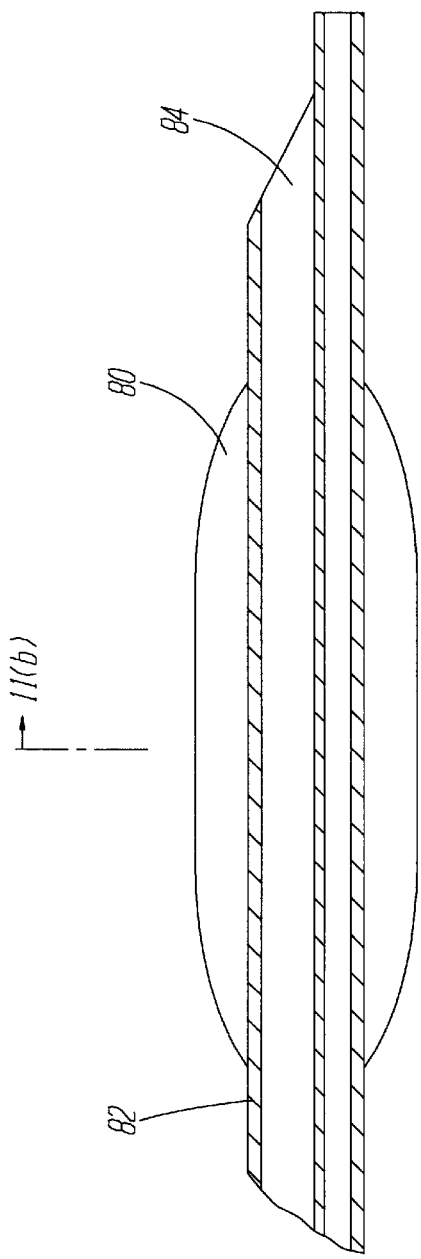
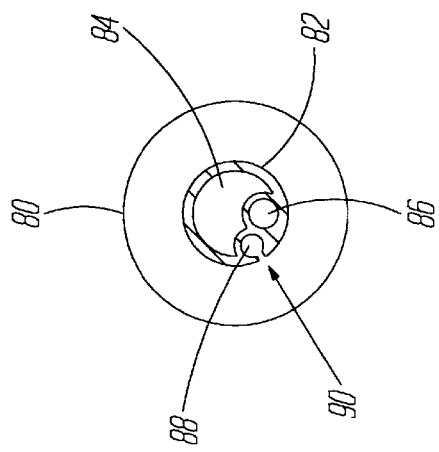
FIG. 11(a)
FIG. 11(b)

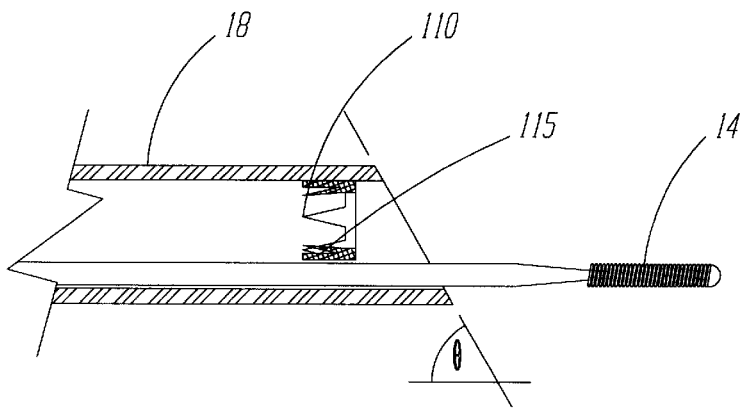
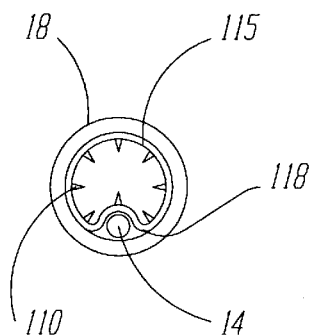
FIG. 12a                FIG. 12b
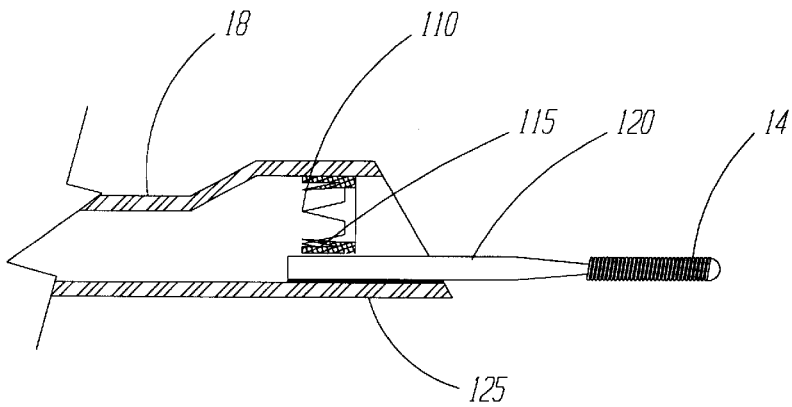
FIG. 13
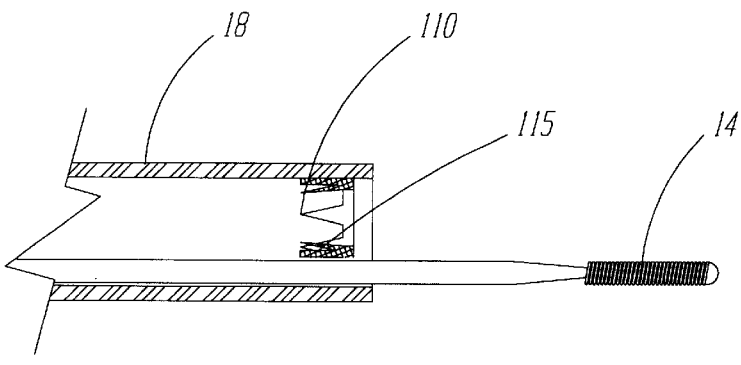
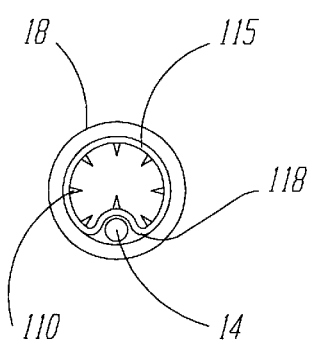
FIG. 14a                FIG. 14b

PERCUTANEOUS ASPIRATION CATHETER SYSTEM

CROSS REFERENCE TO RELATED APPLICATIONS

This application is a continuation in part of U.S. patent application, Ser. No. 08/449,203 filed on May 24, 1995 now U.S. Pat. No. 5,827,229 and entitled PERCUTANEOUS ASPIRATION THROMBECTOMY CATHETER SYSTEM, the entire disclosure of which is hereby incorporated by reference.

FIELD OF THE INVENTION

This invention relates to a device used to break up and extract blood clots or thrombi which form within blood vessels. More particularly, this invention relates to a device adapted to break up and extract clots or thrombi which may form within a coronary artery comprising an improved percutaneous aspiration thrombectomy catheter system.

BACKGROUND OF THE INVENTION

Approximately 1.2 million Americans suffer heart attacks each year. A large percentage of the heart attacks are caused by blood clots or thrombi which form within the coronary arteries. A thrombus is nature's way of stemming the loss of blood from its pipeline system by corking off an opening into the vascular tree. The biochemical process which results in thrombus formation is not fully understood. However, in simple terms, injury to the vascular wall releases chemicals which lead to conversion of soluble, circulating fibrinogen molecules into a polymeric structure of fibrin. The fibrin structure is insoluble and arranges itself into a three dimensional network of meshed strands which entraps red blood cells. The individual strands are approximately 0.2 microns in diameter and the mesh size is approximately 1 micron. Accordingly, five micron red blood cells are easily trapped within the three dimensional "net".

When a thrombus forms, it effectively stops the flow of blood through the zone of formation. If the thrombus extends across the interior diameter of an artery, it cuts off the flow of blood through the artery. If one of the coronary arteries is 100% thrombosed, the flow of-blood is stopped in that artery resulting in a shortage of oxygen carrying red blood cells to supply the muscle (myocardium), of the heart wall. Such a thrombosis is unnecessary to prevent loss of blood but can be undesirably triggered within an artery by damage to the arterial wall from atherosclerotic disease. Thus, the underlying disease of atherosclerosis may not cause acute-oxygen deficiency (ischemia) but can trigger, acute ischemia via induced thrombosis. Similarly, thrombosis of one of the carotid arteries can lead to stroke because of insufficient oxygen supply to vital nerve centers in the cranium. Strokes can also be caused by an embolus which has formed and then is dislodged from an upstream blood vessel or the heart itself. It is carried by flowing blood to a vessel supplying the brain where it lodges in the vessel, blocking the blood flow and triggering a stroke. These emboli may consist of thrombus, atheroslerotic plaque or a combination of the two. They are typically older and harder than fresh thrombus and resist the action of thrombolytic drugs.

Oxygen deficiency reduces or prohibits muscular activity, can cause chest pain (angina pectoris), and can lead to death of myocardium which permanently disables the heart to some extent. If the myocardial cell death is extensive, the heart will be unable to pump sufficient blood to supply the body's life sustaining needs. The extent of ischemia is affected by many factors, including the existence of collateral blood vessels and flow which can provide the necessary oxygen.

Coronary artery bypass graft (CABG) surgery is a surgical method for bypassing coronary arteries which, because of narrowing or obstruction, are unable to supply adequate oxygen to heart muscle. In recent years, direct administration of chemical lysing agents into the coronary arteries has shown to be of some benefit to patients who have thrombosed coronary arteries. In this procedure, a catheter is placed immediately in front of the blockage and a drip of streptokinase is positioned to be directed at the upstream side of the thrombus. Streptokinase is an enzyme which is able in time to dissolve the fibrin molecule. This procedure can take several hours and is not always successful in breaking up the thrombus. Furthermore, it can lead to downstream thrombus fragments (emboli) which can lead to blockage of small diameter branches. Auth, U.S. Pat. No. 4,646,736, discloses a thrombectomy device that permits rapid removal of an obstructive thrombus. However, the device is characterized by small catheter tip size and thus is unable to exert significant total force on clot masses. Also, a clot which is not in good position of purchase on a vessel wall in the "line of fire" of the rotating wire is not fibrinectomized. This is especially true of clots floating free in the blood stream, since it is virtually impossible to revolve within these clots in the absence of a constraint such as fingers.

Further disadvantages to this thrombectomy device include the difficulty of keeping the clot in the space above the wire during all degrees of rotation as the wire is moved sideways during rotation, which is sometimes necessary to sweep the arterial lumen. In fact, sweeping out an entire arterial lumen with a rotating wire is virtually impossible in all but the smallest, i.e., less than 1.5 mm diameter, arteries. An additional and serious possible disadvantage is that fragments of the clot may be embolized downstream.

Therefore, there has been a definite need for a thrombectomy device that can be more effective in sweeping arteries, in removing emboli that are free floating or not perfectly positioned, and in minimizing fragmentation of clots. These and other objects of the invention will become apparent from the following discussion of the invention

SUMMARY OF THE INVENTION

The present invention provides for an improved system for removing thrombus from blood vessels which includes the following components:

- a catheter having proximal and distal ends, designed to be advanced through a hemostasis valve and guide catheter and over a guide wire for placement of its distal end at the thrombus, the catheter having at least one lumen passing from the proximal to the distal end;
- the catheter having a guide wire retaining means, which retains the guide wire within the catheter in a peripheral or non-centered part of the catheter cross-section. The distal tip of the catheter is angled back from the guide wire retaining means to allow the catheter to easily follow the guide wire around tight bends and across restrictions;
- suction means in fluid communication with the proximal end of the catheter for providing vacuum down the catheter lumen to the distal tip, for drawing thrombus into the lumen; and the lumen terminating in and angled tip at the distal end of the catheter, the angled tip improving the removal of thrombus adhering to the vessel wall and reducing clogging of the hole with thrombus.

In another embodiment of the present invention, an improved thrombectomy catheter and method of use is disclosed. The catheter has barbs located near the distal end. The barbs may be attached to the catheter or integrally formed with a radio opaque ring and thereby also serve as a marker band. The ring may have a reverse bend which provides a channel to retain a guide wire. The barbs provide safety in that any particles entering the catheter can not float out. The barbs further provide a means of removing pieces of thrombus which are larger than the diameter of the catheter and which may be too hard to deform or break apart and be drawn through the catheter.

BRIEF DESCRIPTION OF THE DRAWINGS

FIG. 5(a) is a schematic representation of a preferred embodiment of a percutaneous aspiration thrombectomy catheter system according to the present invention with a two lumen configuration;

FIG. 5(b) is a cross-section of the percutaneous aspiration thrombectomy catheter depicted in FIG. 5(a);

FIG. 5(c) is another cross-section of the percutaneous aspiration thrombectomy catheter depicted in FIG. 5(a);

FIG. 7(a) is a cross-sectional representation of a single lumen design of a necked down distal tip for a percutaneous aspiration thrombectomy catheter depicted in FIG. 5(a) showing the location of the proximal entry of the guidewire at the distal exit point of the guidewire;

FIG. 7(b) is a longitudinal cross-section of the single lumen design for a necked down distal tip for the percutaneous aspiration thrombectomy catheter shown in FIG. 7(a) without the insertion of the guidewire;

FIG. 7(c) is a side view of the single lumen design for necked down distal tip for the percutaneous aspiration thrombectomy catheter shown in FIG. 7(a) without the insertion of the guidewire;

FIG. 7(d) is a distal end view of the embodiment shown in FIG. 7(c);

FIG. 9(a) is a schematic representation of the tip design of a preferred embodiment of a percutaneous aspiration thrombectomy catheter system according to the present invention with a two lumen configuration and a barb with two points attached to the catheter tip with the barb points oriented distally;

FIG. 9(b) is a plan view of the barb depicted in FIG. 9(a);

FIG. 11(a) is a schematic representation of the tip design of a preferred embodiment of a percutaneous aspiration thrombectomy catheter system according to the present invention with a two lumen configuration and an expandable balloon attached to the catheter tip-near to the distal end; and FIG. 11(b) is a cross-sectional representation of the distal tip depicted in FIG. 11(a).

FIG. 12(a) is a partially cross-sectioned side view of another embodiment of the percutaneous aspiration thrombectomy catheter system.

FIG. 12(b) is an end view of the embodiment of FIG. 12(a).

FIG. 13 is a partially cross-sectioned side view of another embodiment of the percutaneous aspiration thrombectomy catheter system.

FIG. 14(a) is a partially cross-sectioned side view of further embodiment of the percutaneous aspiration thrombectomy catheter system.

FIG. 14(b) is an end view of the embodiment of FIG. 14(a).

DETAILED DESCRIPTION OF THE INVENTION

Figure 3B:
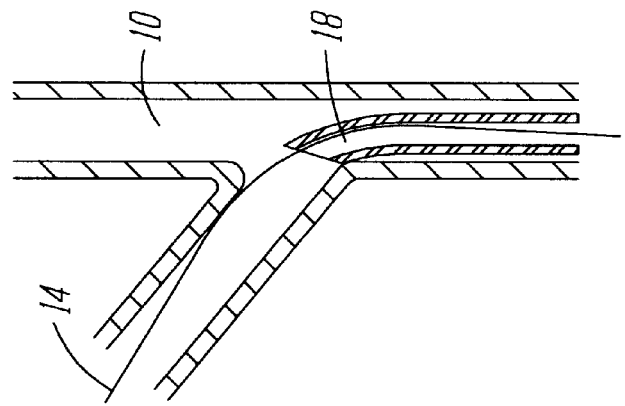
FIG. 3(b) is a schematic representation of a bifurcated blood vessel having a constrained angled tip catheter and guidewire inserted at the point of bifurcation with the angled tip of the catheter in another orientation.

According to the invention, a system for removing thrombus from blood vessels comprises a catheter having proximal and distal ends, designed to be advanced through a hemostasis valve and guide catheter and over a guidewire for placement of its distal end at the thrombus, the catheter having at least one lumen passing from the proximal to the distal end, and a guidewire retaining means, which retains the guidewire within the catheter in a peripheral or non centered part of the catheter cross section. The distal tip of the catheter is angled back from the guidewire retaining means to allow the catheter to follow the guidewire around tight bends and across restrictions easily. Also, there is suction means in communication with the proximal end of the catheter for providing vacuum down the catheter lumen to the distal tip, for drawing thrombus into the lumen, and the lumen terminates in the angled tip at the distal end, the angled tip improving the removal of thrombus adhering to the vessel wall and reducing clogging of the hole with thrombus.

Various prior art references on thrombectomy aspiration catheters address the use of plain, single lumen catheters with a blunt tip over a conventional guidewire. In some cases the catheters taught there may have side holes (such as, for example, drug infusion catheters). In-vitro testing has established that single lumen, round bore catheters need to be at least 0.042" i.d. to effectively remove a thrombus with a 0.009" guidewire down the middle. When such catheters were placed in a "heart model", it was found that it was sometimes very difficult to maneuver such a catheter over the wire at a bifurcation. The blunt tip tended to advance straight and would catch at the bifurcation. Adding an angled tip to the catheter helped in negotiating the bend if the tip was on the inner radius of the curvature. If it was on the outside, it increased the tendency to snag at the bifurcation. As will be seen, adding a means to capture the guidewire on one side of the catheter and tapering from that point made it possible to always negotiate a right bend or bifurcation.

Vacuum is provided using a small diaphragm pump which maintains a steady vacuum of about 550 millimeters of Mercury vacuum. The use of a pump makes it easy to advance the catheter tip through the thrombus with a steady vacuum level. Most of the previous clinical use of thrombectomy catheters used suction applied with a syringe, It has been found that it is difficult to advance the catheter while maintaining steady vacuum with the syringe.

The angled tip provided for in the present invention provides a greater cross-sectional area for the thrombus to enter the catheter, increasing the total force (Force=Pressure X Area) which is applied to the thrombus, increasing the amount and rate of thrombus removal and reducing the tendency to clog.

Various additional features are contemplated and may be optionally incorporated into the device of the present invention to improve its overall efficiency and workability. For example, an exit point for the guidewire allows the guidewire to continue outside of the catheter in the proximal section, allowing the catheter and guidewire to separately pass through the hemostasis valve.

It has been found that optimal tracking of the relatively large bore thrombectomy catheter over the small guidewire works best if the wire is held at the outer wall of the catheter tip and the tip is angled back from that point. However, to simplify sealing around the guidewire it is generally easiest if the guidewire and catheter are passed through the hemostasis valve separately. This eliminates the need for a separate seal around the guidewire at the proximal end of the catheter. This is advantageous, as was shown when an embodiment of the present invention was tested with a seal at the proximal end of the catheter through which a guidewire was passed. To advance the catheter over the guidewire with the vacuum on, the guidewire seal had to be loosened. Air was immediately pulled through the seal and into the catheter and rapidly filled the blood collection bottle. Also, there was a lower level of vacuum in the inner lumen at the catheter tip. The presence of air in the catheter can also be a problem if it is desired to infuse medicants through the catheter.

Since coronary thrombi are often initiated by a lesion on the vessel wall, it is sometimes advantageous to dilatate the lesion with a balloon catheter, thereby reducing the constriction and reducing the chances for another thrombotic event. Many examples of these devices are known to the art. To facilitate this dilatation procedure, an expandable dilatation balloon may be incorporated integral to thrombectomy catheter at or near the distal tip. This allows the operator to easily dilatate the lesion before or after aspirating the thrombus utilizing a single device.

A situation occasionally occurs when a large, very firm thrombus is aspirated into a catheter tip but is not fragmented and withdrawn down the catheter. In this situation, there is a need to positively retain the thrombus within the catheter tip. To accomplish this a barb incorporating one or more-points can be placed within the catheter lumen at the distal tip. By orienting the points proximally, the thrombus is effectively retained and prevented from escaping.

Another way to handle this situation is to place a blade within the distal tip of the catheter lumen with the sharp edge facing distally. The blade cuts the large thrombus and allows the pieces to more easily pass through the catheter lumen.

A bottle or bag may be provided between suction means and the catheter for collecting blood and thrombus as it is removed by the suction means. Further, a filter may be provided between the suction means and the catheter to separate the solid thrombus from the liquid blood, said filter preferably being located-within the collecting bottle. The filter provides a convenient way to visualize the amount of clot removed and makes it easy to take a sample for analysis.

A guidewire retaining means may be provided, comprising a second lumen extending proximally from the distal end of the catheter, terminating prior to the point where the catheter passes through the hemostasis valve.

A variation of the device of the present invention wherein the guidewire retaining means comprises a second lumen has both advantages and disadvantages. Advantages include:

no holes penetrating through the main aspiration lumen to reduce vacuum to the tip and suck additional blood through; and slight ease in loading the catheter on the guide wire.

A "partial rapid exchange" design can be accomplished using a long guidewire lumen with a slit from the proximal end, extending to several inches (less than 10 cm) from the distal end. The cardiologist user can load the catheter over the short rapid exchange length guidewire and insert both the wire and catheter through the guide sheath to the coronary arteries. At that point, the guidewire extends distally out of the catheter and through the thrombus. The catheter is then advanced. To remove the catheter, it is withdrawn over the wire to the point where the guidewire lumen is exposed and then the catheter is peeled off of the guidewire as it is withdrawn to the end of the slit. The last two inches are then pulled off. At this point another rapid exchange catheter can be advanced over the guidewire but not another thrombectomy catheter. Of course, the thrombectomy catheter can be used with any standard length guidewire.

The main disadvantage of the two lumen design is that a slightly larger diameter is required due to the presence of the added internal wall.

The proximal end of the second guidewire lumen may be provided with a slit for a portion of its length from the proximal end toward the distal end to allow for the peeling of the catheter from the guidewire, as the catheter is removed from the vasculature over the guidewire. Also, the device of the present invention may be configured as a single lumen catheter where the guidewire retaining means is comprised of two holes in the lumen, one at the distal end and one intermediate between the distal and proximal ends allowing the guidewire and catheter to pass separately through the hemostasis valve.

This latter design is the simplest to manufacture but it has some functional problems as described above for the double lumen configuration.

The end of the catheter can be necked down for a distance before the guidewire exit hole at the distal end of the catheter. The reason for this necking down is that it allows the guidewire to be retracted into the catheter without losing placement in the guidewire hole. This technique is often used when the cardiologist is initially inserting the guidewire and catheter through the hemostasis valve. Retracting the guidewire into the catheter protects the delicate guidewire tip while advancing across the hemostasis valve which can damage the tip if exposed.

The distal end of the catheter may be offset from the catheter center line, improving the removal of thrombus adhering to the vessel wall when the catheter is rotated around the guidewire. This is an improvement which may be incorporated into a catheter intended for use in larger vessels. Reinforcing the wall of the catheter with metal or plastic braid substantially increases the torsional strength and kink resistance of the catheter yet maintains longitudinal flexibility for placement of the catheter within tortuous vessels.

The suction means may be attached to the catheter with tubing, the size and length of said tubing being selected to reduce the flow of blood due to friction flow losses, reducing blood removal from the patient without becoming clogged from aspirated thrombus particles. This concept was demonstrated, by using a 1/8" i.d. tube, 10 feet long, connecting the vacuum pump to a catheter, to aspirate 125 cc of blood while removing a typical thrombus. By reducing the tubing diameter to 1/16" i.d., the amount of blood aspirated was reduced to approximately 50 cc with no loss of efficacy. There is an obvious benefit to minimizing the amount of blood lost by the patient.

A valve may be located between the catheter and suction means to shut off or regulate the vacuum level delivered to the catheter. This represents a convenient way for the cardiologist to regulate vacuum without having to have someone turn the pump on and off.

The collection bottle may be provided with a window, or clear portion, through which any clot collected in the filter may be visualized. An access port located above the clot filter may be provided, through which saline or other washing solutions maybe directed onto the thrombus to improve visualization and aid in discernment of clot fragments.

A push-pull transport system as described in U.S. Pat. No. 4,561,807, incorporated herein by reference, may be incorporated into the suction means. The surfaces of all components in blood contact may be coated with an antithrombogenic material such as heparin complex, hirudin or other clot-inhibiting chemical. The purpose of such a coating is to ensure that the collected clot came from the treated blood vessel and was not formed from the liquid blood.

In comparison to some types of therapeutic catheters, such as balloon dilatation catheters, the percutaneous aspiration catheter has a relatively large cross-section. This is required to prevent occlusion by the aspirated thrombus. To assist in negotiating the catheter across restrictions in a blood vessel the distal portion may be coated with a lubricious or low friction coating such as polyvinylpyrrolidone hydrogel. Use of such a catheter in the coronary arteries of animal subjects has reduced the difficulty in penetrating a thrombus. One advantage of using a hydrogel coating for this purpose is that antithrombotic material such as heparin may be incorporated into the hydrogel coating, providing both benefits with one coating application. The low friction-coating may also be placed on the inside of the catheter lumen to reduce the possibility of the thrombus sticking within it.

The internal flow cross-section of the catheter and connecting tubing may be provided with a progressively increasing area to the thrombus filter to prevent thrombus from plugging at any point.

Smooth surfaces and joints may be provided in the catheter and connecting tubing to prevent thrombus from snagging and catching at any corners or rough edges, preventing them from reaching the thrombus filter.

Figure 2:
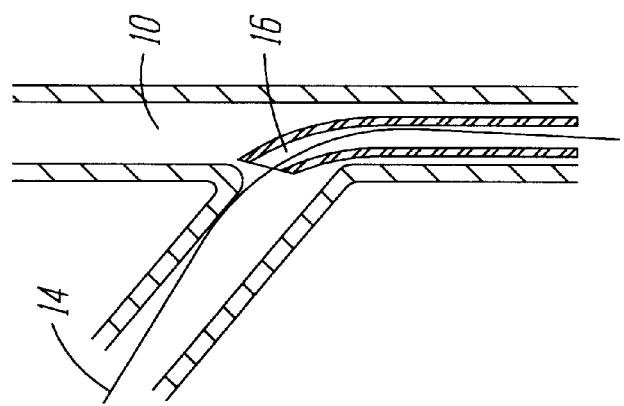
FIG. 2 is a schematic representation of a bifurcated blood vessel having a catheter with an unconstrained angled tip and guidewire inserted therein at the point of bifurcation.
Figure 1:
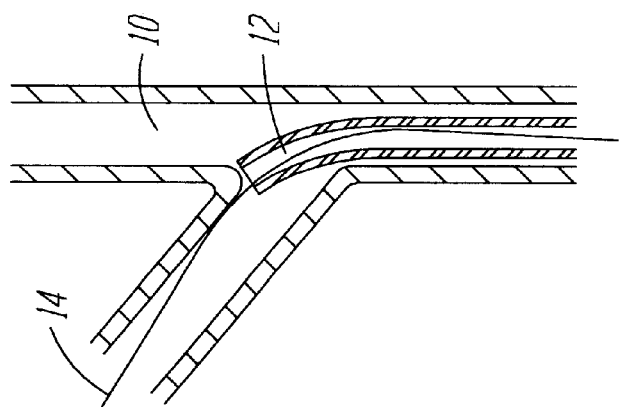
FIG. 1 is a schematic representation of a bifurcated blood vessel having a blunt tip catheter and guidewire inserted at the point of bifurcation.

The invention can perhaps be better understood by making reference to the drawings. with reference to FIG. 1, schematic representation of a bifurcated blood vessel 10 is depicted wherein a blunt tip catheter 12 and guidewire 14 are inserted at the point of bifurcation showing the catheter lodged at the point of bifurcation. FIG. 2 is a schematic representation of bifurcated blood vessel 10 and an unconstrained angled tip-catheter 16 and guidewire 14, shown inserted at the point of bifurcation and also showing the catheter lodged at the point of bifurcation.

Figure 3A:
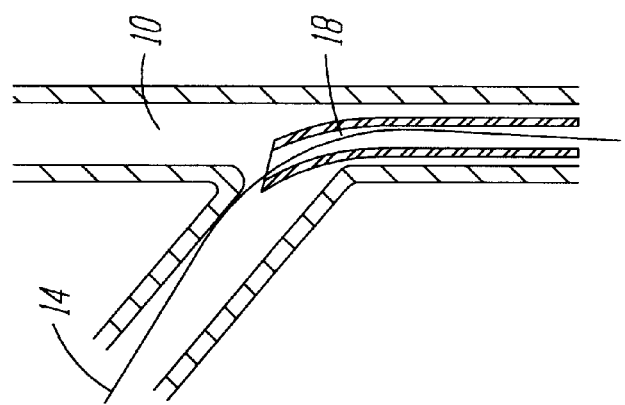
FIG. 3(a) is a schematic representation of a bifurcated blood vessel having a constrained angled tip catheter and guidewire inserted at the point of bifurcation with the angled tip of the catheter in one orientation.

With reference to FIG. 3(a), constrained angle tip catheter 18 and guidewire 14 are inserted into bifurcated blood vessel 10. This shows the smooth passage of the constrained angled tip catheter/guidewire through the point of bifurcation. FIG. 3(b) is a schematic representation of a bifurcated blood vessel 10 having a constrained angled tip catheter 18 in an alternative orientation and an inserted constrained guidewire 14 at the point of bifurcation. Also shown is the smooth transition of the catheter guidewire through the point of bifurcation.

Figure 4:
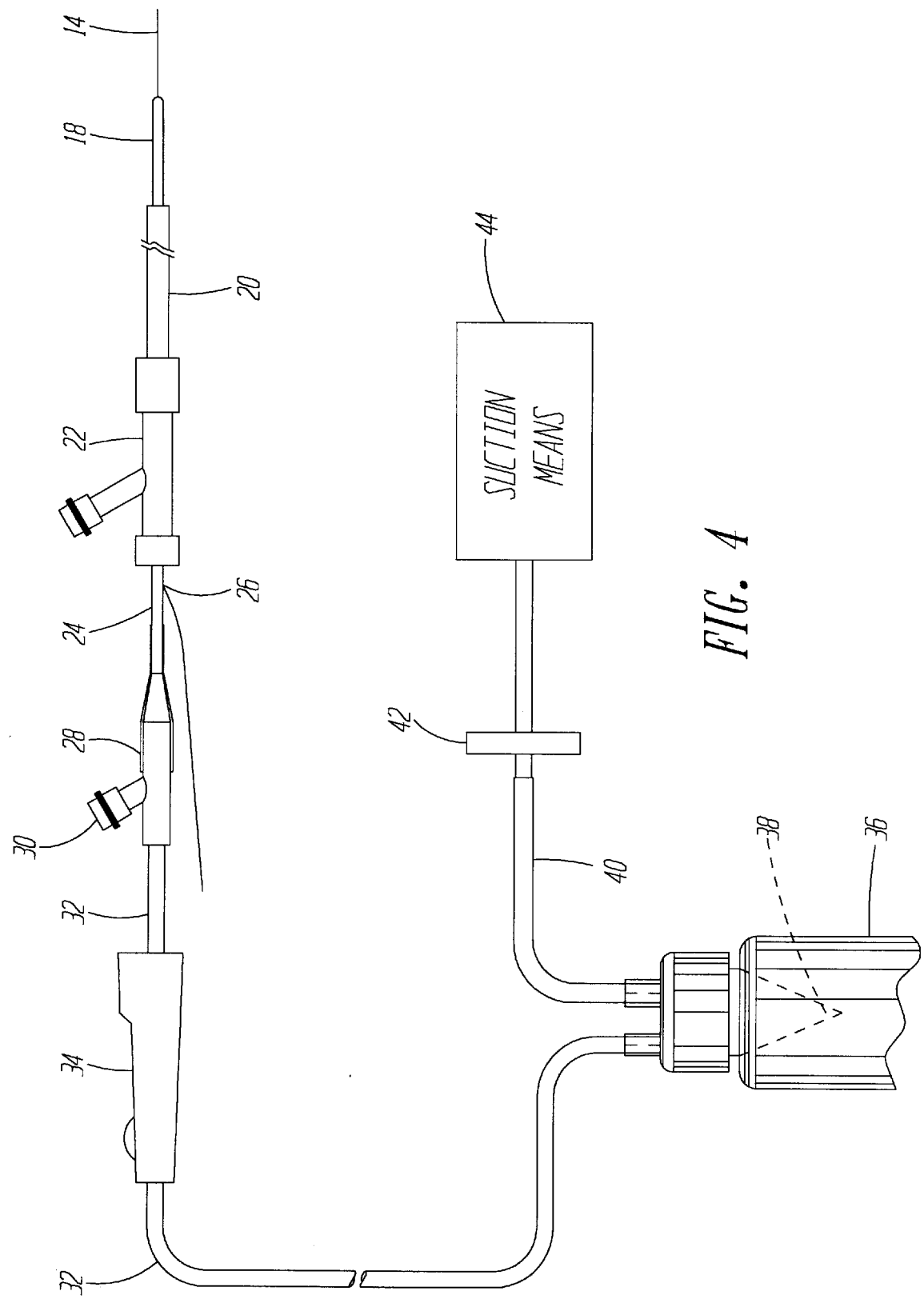
FIG. 4 is a schematic representation of a preferred embodiment of percutaneous aspiration thrombectomy catheter system. according to the present invention.

FIG. 4 comprises a schematic representation of a preferred arrangement of a complete percutaneous aspiration thrombectomy catheter system according to the present invention. A constrained angled tip catheter 18 has a guidewire 14 passing through the constrained distal tip of said catheter guidewire arrangement passing through guide catheter 20, which in turn is contained within a hemostasis valve 22 through which the catheter guidewire exits at the proximal end 24. Proximal to the exit of the catheter guidewire from the hemostasis valve is a guidewire exit port 26. The proximal end of the catheter is provided with a transitional connecting means 28 which is provided with an auxiliary Luer port 30. The proximal end of the transitional connecting means is attached to a connecting tubing 32 which passes through a clamp 34 before entering a collection bottle 36, which is provided with a filter means 38 to separate thrombus from blood which has been aspirated from a patient's artery. The outlet port of the collection bottle is provided with additional connecting tubing 40 which passes through a hydrophobic barrier filter 42 prior to entering the suction end of a suction means 44.

FIG. 5(a) represents a preferred embodiment of a percutaneous aspiration thrombectomy catheter system according to the present invention, where a two lumen configuration is depicted showing the catheter 18 having a guidewire 14 passing through a separate guidewire lumen 42 which is formed as part of the catheter 18. The proximal end of the catheter passes through a hemostasis valve 22 and subsequently enters a transitional connection means 28 having an auxiliary Luer port 30, the proximal end of which connection means 28 is provided with connecting tubing 32.

A cross-sectional of the proximal portion of the catheter 18 is depicted in FIG. 5 (b) showing the internal guidewire lumen 46, which in this section of the catheter is provided with a slit 48 for easy removal of the guidewire.

The cross-section of the distal portion of the catheter 18 is depicted in FIG. 5(c) showing the internal guidewire lumen 46, which in this section of the catheter is not provided with a slit.

Figure 6A:
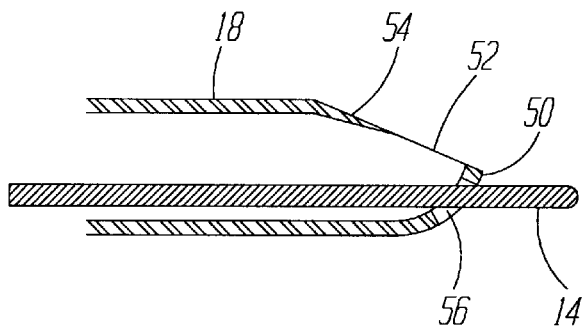
FIG. 6(a) is a schematic representation of the tip design of a single lumen percutaneous aspiration thrombectomy catheter according to the present invention showing a variation wherein the distal tip is punched to provide a hole through which the guidewire is inserted.

FIG. 6(a) is a schematic representation of the tip design for a single lumen percutaneous aspiration thrombectomy catheter system according to the present invention, showing the distal end of the catheter 18 having a bent upward distal tip 50 and a thrombus entry opening 52 located in the angled portion of the distal end 54. The bent up position of the distal tip is provided with a guidewire opening 56 through which the guidewire 14 passes.

Figure 6B:
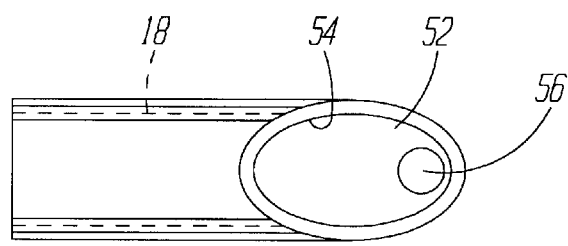
FIG. 6(b) is a plan view of a schematic representation of the distal tip depicted in FIG. 6(a)

In FIG. 6(b) a top plan view of a schematic representation of the distal end of the catheter 18 shows the angled portion of the distal end 54, the thrombus entry opening 52, and the guidewire entry opening 56.

Figure 6C:
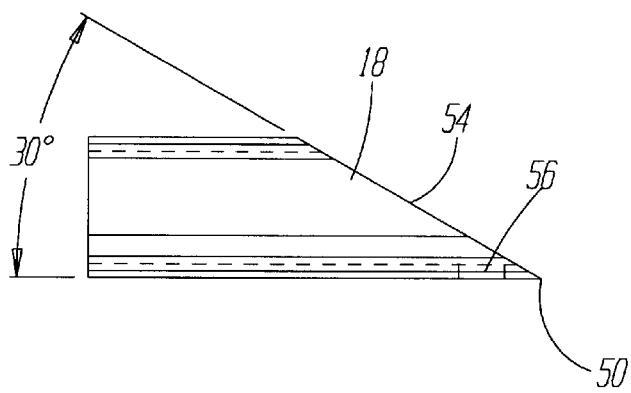
FIG. 6(c) is a side view of the distal tip depicted in FIG. 6(a) prior to the formation of the bent tip.

With reference to. FIG. 6(c) a lateral partly cross-sectional view of the distal-tip of the catheter 18 of FIG. 6(b) is depicted showing the angle orientation of the angled distal tip 50 and the location of the guidewire entry opening 56 prior to the formation of the bent tip in the upward position. The material of catheter 18 is sufficiently flexible that the distal tip 50 will lie flat prior to insertion of guidewire 14. However, if catheter 18 is made of more rigid material, the distal tip 50 will be bent upward as in FIG. 6(a), without guidewire 14 present.

Figure 6D:
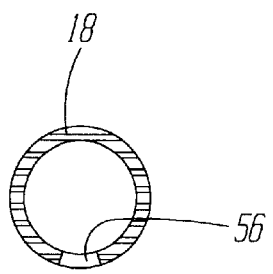
FIG. 6(d) is an end view of the distal tip depicted in FIG. 6(c)

FIG. 6(d) is an end, distal view of the distal tip according to FIG. 6(c) showing the catheter 18 and the location of the guidewire entry opening 56 prior to the tip being bent upward.

With reference to FIG. 7(a) a cross-sectional representation of a single lumen catheter 18 is shown which depicts a necked down distal tip 58 and the guidewire 14 passing through the distal end of said necked down distal tip and exiting through the proximal guidewire exit opening 26.

With reference to FIG. 7(b) a longitudinal cross-section of the single lumen design of the percutaneous aspiration thrombectomy catheter system according to the present invention is shown depicting the catheter 18 the necked down distal tip 58 of the catheter, and the thrombus entry opening 52.

FIG. 7(c) is a lateral view of the single lumen design of the percutaneous aspiration thrombectomy catheter system and the necked down distal tip 58, while FIG. 7(d) is a distal end view.

Figure 8:
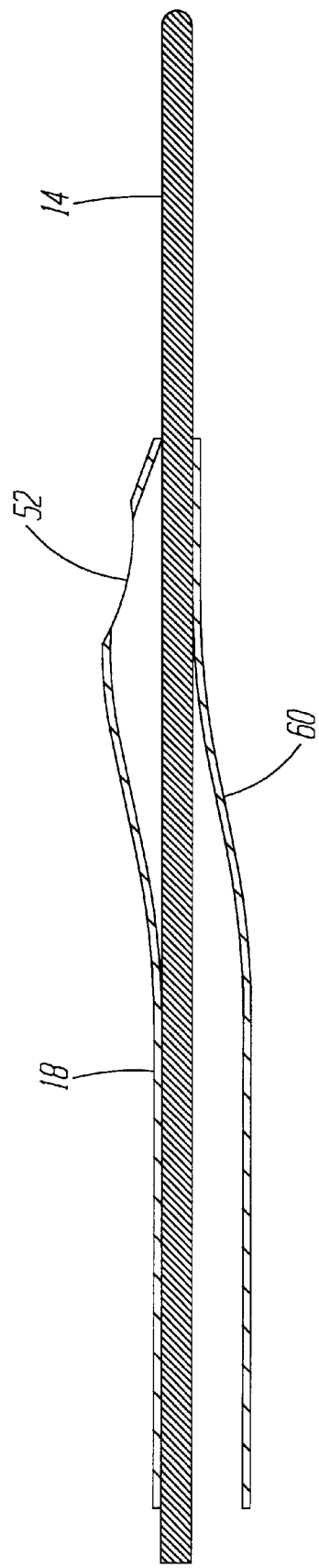
FIG. 8 is a cross-sectional representation of a single lumen off-set tip design for the percutaneous aspiration thrombectomy catheter according to FIG. 5(a) showing a distal guidewire exit hole and a thrombus entry port located in the off-set section of the distal tip.

With reference to FIG. 8 a cross-sectional representation of a single lumen off-set tip design for the percutaneous aspiration thrombectomy catheter system according to FIG. 5(a) is depicted showing the catheter 18 guidewire 14 thrombus entry hole 52 and the distal tip having a skewed orientation 60.

The embodiments of the invention shown in FIGS. 9(a) to 11(b) represent variations of the embodiment depicted in FIGS. 5(a) to 5(c). In FIG. 9(a) catheter 18 comprises extended guidewire lumen 58, fixed concentric to which is barb 60. Barb 60 has a proximally extending section 62, which has one or more, preferably two, pointed members 63 to engage thrombus. Pointed members 63 extend slightly into opening 65, sufficient to be effective to retain thrombus as desired but not to block opening 65.

Figure 10A:
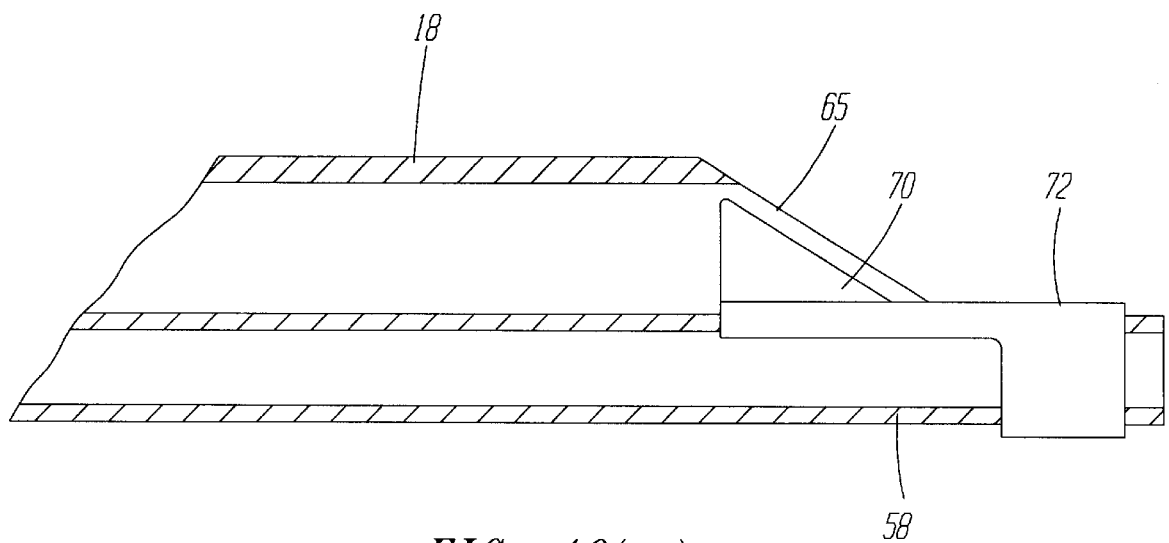
FIG. 10(a) is a schematic representation of the tip design of a preferred embodiment of a percutaneous aspiration thrombectomy catheter system according to the present invention with a two lumen configuration and a cutting-blade attached to the catheter tip with the blade bisecting the thrombus aspiration lumen.
Figure 10B:
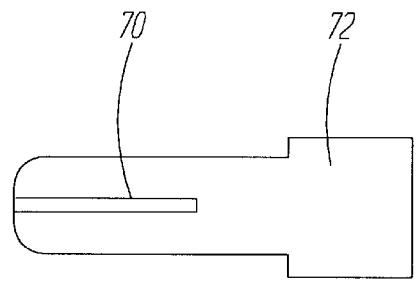
FIG. 10(b) is a plane view of the blade depicted in FIG. 10(a)
Figure 10C:
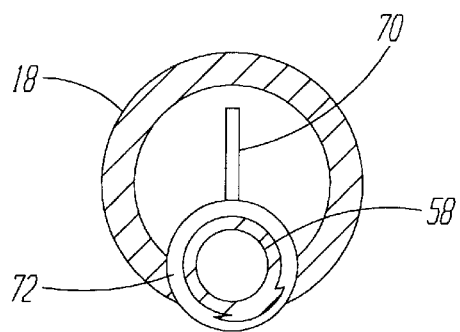
FIG. 10(c) is an end view of the distal tip depicted in FIG. 10(a)

Another arrangement is shown in FIGS. 10(a) to 10(c), where a cutting blade 70 is positioned on blade holder 72 blade holder 72 is fixedly concentric to extended guidewire lumen 58. The purpose of blade 70 is to bisect large thrombi that might enter opening 65.

Barb 60, blade 70, and blade holder 72 are preferably fashioned from rigid materials. Useful such materials include suitably rigid polymers and co-polymers and medically acceptable metals.

The embodiment shown in FIGS. 11(a) and 11(b) has a dilatation balloon 80 concentrically positioned around catheter 82. Catheter 82 comprises three lumens, namely, suction lumen 84, guidewire lumen 86, and inflation lumen 88. Balloon 80 is in fluid communication with inflation lumen 88 by means of any conventional configuration or arrangement, such as one or more inflation port 90.

Manufacture of the catheters herein, including the catheter of FIGS. 11(a) and 11(b), is within the skill of any art skilled person. For example, the balloon can be manufactured and/or attached in conventional manner.

FIGS. 12–14 depict several alternative embodiments of the percutaneous aspiration catheter. In general, each of these embodiments have barbs which are mounted inside a catheter near the distal end. Barbs provide the added advantage of trapping material within the catheter. Barbs also prevent pieces of thrombus from floating out of the catheter and further provide an apparatus for removing emboli which are larger than the distal end of the catheter. Variations on these embodiments include an embodiment with a flared distal end to the catheter (See FIG. 13). The flared distal end has the advantage of providing a larger diameter capture opening. The flared distal end also allows room for the placement of barbs within the tip without restricting the removal of particles. Any particles that are small enough to pass through the catheter lumen will not be impeded by the barbs.

Another embodiment has an angled tip, where the angled tip provides a less traumatic tip and also creates a larger cross-sectional area to the distal opening of the catheter (See FIGS. 12a and 14a). Another embodiment is disclosed that may be used over a guide wire (See FIGS. 12a and 14a). Finally, an embodiment with a fixed guide wire tip at the distal end of the catheter is disclosed (See FIG. 13). The fixed guide wire tip provides some of the advantages of a guide wire while also providing a maximum cross-sectional open lumen for thrombus removal. It is possible to make any of these embodiments in a fixed wire, over the wire, or no wire configuration. Further, any of these embodiments may have a straight tip, an angled tip, or a flared tip. All materials, dimensions, processes of manufacture, features, and advantages previously described may also apply to the following embodiments except as described hereafter.

FIG. 12a depicts an embodiment of the percutaneous aspiration catheter where barbs 110 are positioned within the distal portion of catheter 18 and oriented such that the sharp part of the barb 110 is pointed proximally. Barbs 110 may be made separately and attached to the interior of catheter 18 or integrally formed in a ring 115. Barbs 110 may be machined into ring 115 by milling or laser cutting and are preferably formed by electrical-discharge machining. It is very important that barbs 110 be as sharp as possible. Therefore post polishing or sharpening of barbs 110 may be preferred after barbs 110 are machined into ring 11 5. Ring 115 may further be bent into a noncircular shape, as shown in FIG. 12b, where a reverse bend 118 in the circumference of ring 115 may act as a guide wire retainer. Reverse bend 118 retains guide wire 14 near the edge of the interior of catheter 18 and therefore provides the maximum continuous cross-sectional area for thrombus to travel through catheter 18.

Ring 115 may be made of any medical grade metal, and is preferably a radio-opaque alloy, such as a platinum-iridium alloy consisting of 90% platinum and 10% iridium. As a radio opaque alloy, ring 115 may also serve as a marker band facilitating radiographic visualization. Ring 115 may be mounted near the distal opening of catheter 18. Preferably ring 115 is adhesively bonded to the interior of catheter 18. Adhesives that may be used include cyanoacrylates and epoxies.

Catheter 18 may be used with a guide wire 14, without a guide wire, or in a fixed wire configuration. Catheter 18 may have a single layer or plurality of layers. In a preferred embodiment catheter 18 may be made from three layers where the inner layer is made of PTFE and has a wall thickness of about 0.003 inches. The intermediate layer is a braid of metal or plastic filaments with a wall thickness of about 0.002 inches. The braid may have a continuous or variable pick count. The outer layer is a thermoplastic such as polyurethane with a wall thickness of about 0.002 inches. When using catheters 18 with as larger as an outside diameter of 0.039 inches, the flared tip may be as large as 0.052 inches allowing barbs 110 to be bent inward 0.0065 inches without restricting the size of particles that may be drawn into catheter 18.

FIG. 13 shows another embodiment of the percutaneous aspiration catheter where the distal end of catheter 18 is larger in diameter than the body of catheter 18. This flared portion 125 provides a larger working area for the suction end of catheter 18. Flared portion 125 preferably is formed by stretching the distal portion of catheter 18 over a hot mandrel. However, in embodiments where a layer of braid is incorporated into the construction of catheter 18, a separate flared portion 125 may be constructed and adhesively attached to the distal end of catheter 18.

FIG. 13 also shows a fixed guide wire tip 120 which is mounted inside the distal end of catheter 18 and extends out of the distal end. Guide wire tip 120 has a spring tip 14, as is commonly known in the art. Guide wire tip 120 may fit into a reverse bend 118 as in the embodiment shown in FIG. 12b. Guide wire 120 is adhesively bonded to catheter 18. Guide wire tip 120 provides guidance for catheter 18 and is helpful in negotiating the tortuous vasculature. Since guide wire tip 18 is bonded to catheter 18 near the distal end but does not extend proximally of the bond, guide wire tip 18 does not block most of the fluid path within catheter 18. This guide wire tip configuration provides the ability to negotiate tortuous vessels and still have the high suction capability of embodiments of the percutaneous aspiration catheter that do not have a wire.

Both of the embodiments of FIGS. 12a and 13 show an angled distal end of catheter 18 where the guide wire 14 or the fixed guide wire tip 120 is preferably positioned to correspond to the distal-most portion of the angled end of catheter 18. As previously described, an angled tip provides better advancement around corners and through bifurcated vessels. FIG. 12a depicts the distal opening of catheter 18 having an angle θ with respect to a line parallel to the atherefore heter 18. The distal opening therefore must also be oriented at an angle θ with respect to the axis of catheter 18 and must be from 0–90°. FIG. 14a shows yet another embodiment of the percutaneous aspiration catheter where the distal end of catheter 18 is flat and FIG. 14b depicts a side view of the embodiment of FIG. 14a.

In use, barbed embodiments of the percutaneous aspiration catheter have several added benefits. During normal aspiration barbs 110 provide a safety mechanism where embolus that is drawn into catheter 18 can not float out of the end of catheter 18. In addition, barbs 110 may be particularly useful in removing particles which are larger than the diameter of catheter 18. In cases like these a portion of a large piece of thrombus may be drawn into the end of catheter 18 and caught by barbs 110. Even though the piece of thrombi is too large to flow through catheter 18 it can then be removed from the body by removing catheter 18.

It will be further apparent to one skilled in this art that the improvements provided for in the present invention, while described with relation to certain specific physical embodiments also lend themselves to being applied in other physical arrangements not specifically provided for herein, which are nonetheless within the spirit and scope of the invention taught here.

I claim:

1. A percutaneous aspiration catheter comprising:

a catheter having a proximal end, a distal end, and a lumen therethrough; and a ring mounted within the lumen of the catheter near the distal end, the ring including a plurality of barbs that contact a portion of the material entering the catheter to reduce the likelihood that such material will re-exit the distal end of the catheter while being allowed to move toward the proximal end of the catheter, the ring further including a reverse bend suitable for forming a channel to act as a guide wire retainer.

2. The percutaneous aspiration catheter of claim 1 wherein the ring is made of a radio opaque material.

3. The percutaneous aspiration catheter system of claim 1 wherein portions of the catheter are coated with an anti-thrombogenic coating.

4. The percutaneous aspiration catheter system of claim 1 wherein the distal end of the catheter is coated with a lubricious coating.

5. The percutaneous aspiration catheter of claim 1 further comprising:

a guide wire lumen within the catheter lumen.

6. The percutaneous aspiration catheter system of claim 5 wherein a proximal end of the guide wire lumen is provided with a slit for a portion of the length of the guide wire lumen from a proximal end of the guide wire lumen toward a distal end of the guide wire lumen, the slit allowing for the peeling of the catheter from a guide wire therein.

7. The percutaneous aspiration catheter of claim 1 further comprising:

a wire tip attached to an internal surface of the catheter lumen and extending beyond the distal end of the catheter.

8. A percutaneous aspiration catheter which comprises:

an elongate catheter having a proximal end, a distal end and an aspiration lumen extending therethrough;

means positioned within a distal end of the aspiration lumen the means comprising a ring including a reverse bend and barbs having points that are oriented towards a longitudinal axis of the aspiration lumen and towards the proximal end of the catheter for engaging material that enters the aspiration lumen and preventing the material from re-exiting the distal end while allowing the material to move toward the proximal end.

9. The percutaneous aspiration catheter of claim 8, wherein the barbs are mounted on a ring that is positioned within the aspiration lumen at the distal end of the catheter.

10. The percutaneous aspiration catheter of claim 9, wherein the ring includes a reverse bend that forms a guide wire retainer in the aspiration lumen.

11. An embolectomy method comprising:

providing a catheter having an elongate body, a lumen therethrough, a distal opening, and barbs mounted within the lumen near the distal opening such that at least a portion of material entering the distal end of the catheter contacts some of the barbs so that some material is prevented from exiting the distal end of the catheter while being allowed to move toward the proximal end of the catheter;

advancing the catheter through the vasculature until the distal opening is adjacent a site to be treated; and providing suction at a proximal opening of the catheter.

12. The embolectomy method of claim 11 further comprising;

catching material larger than the diameter of the lumen in the barbs; and removing the catheter from the vasculature while the material remains caught in the barbs.

* * * * *